(12) United States Patent
González et al.

(10) Patent No.: US 6,207,629 B1
(45) Date of Patent: Mar. 27, 2001

(54) CONCENTRATED AQUEOUS BETAINE-TYPE SURFACTANT COMPOSITIONS AND PROCESS FOR THEIR PREPARATION

(75) Inventors: Josep Maria González; María José Bermejo; Rosa María Barceló ; Josep Vilaret; Nuria Siscart, all of Barcelona (ES)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/284,482

(22) PCT Filed: Nov. 5, 1997

(86) PCT No.: PCT/JP97/04024

§ 371 Date: Apr. 22, 1999

§ 102(e) Date: Apr. 22, 1999

(87) PCT Pub. No.: WO98/20093

PCT Pub. Date: May 14, 1998

(30) Foreign Application Priority Data

Nov. 5, 1996 (ES) ........................................ 9602328

(51) Int. Cl.[7] .............................. C11D 1/90; C11D 7/36; C11D 1/04
(52) U.S. Cl. ......................... 510/123; 510/119; 510/237; 510/347; 510/433; 510/469
(58) Field of Search .................................. 510/119, 123, 510/237, 347, 433, 469

(56) References Cited

U.S. PATENT DOCUMENTS

| 3,954,845 | * | 5/1976 | Martinnson et al. | ........... | 260/501.13 |
|---|---|---|---|---|---|
| 4,758,376 | * | 7/1988 | Hirota et al. | ........... | 252/545 |
| 4,861,517 | | 8/1989 | Bade | ........... | 252/546 |
| 5,139,781 | * | 8/1992 | Birtwistle et al. | ........... | 424/401 |
| 5,447,652 | * | 9/1995 | Nozaki et al. | ........... | 252/174.16 |
| 5,464,565 | | 11/1995 | Hamann et al. | ........... | 252/546 |
| 5,789,370 | * | 8/1998 | Thomas et al. | ........... | 510/424 |

FOREIGN PATENT DOCUMENTS

| 19 505 196 | 5/1996 | (DE) . |
|---|---|---|
| 0 353 580 | 2/1990 | (EP) . |
| 06 63 46 | 6/1995 | (EP) . |
| 67 75 09 | 10/1995 | (EP) . |
| 06 47 613 | 1/1998 | (EP) . |
| WO 95/12571 | 5/1995 | (WO) . |
| WO 95/14658 | 6/1995 | (WO) . |
| WO 95/24377 | 9/1995 | (WO) . |

* cited by examiner

Primary Examiner—Yogendra Gupta
Assistant Examiner—Charles Boyer
(74) Attorney, Agent, or Firm—Oblon, Spivak, McClelland, Maier & Neustadt, P.C.

(57) ABSTRACT

A concentrated aqueous betaine surfactant composition consisting essentially of a betaine compound and from 0.5 to 3.5 wt %, based on the total weight of the composition, of at least one fluidizing additive selected from the group consisting of (i) a fatty acid dimer composition and (ii) phosphoric esters of fatty alcohols or polyethoxylated fatty alcohols, the composition containing a solid content of at least 40 wt %, said composition having a reduced viscosity and a low gel point.

9 Claims, No Drawings

CONCENTRATED AQUEOUS BETAINE-TYPE SURFACTANT COMPOSITIONS AND PROCESS FOR THEIR PREPARATION

FIELD OF THE INVENTION

The present invention relates to concentrated aqueous betaine-type surfactant compositions which include, as fluidizing additives, dimers of fatty acids and/or phosphoric esters esters of fatty alcohols or polyethoxylated fatty alcohols which provide the said compositions with reduced viscosity and a low gel point.

STATE OF THE ART

Among the amphoteric type of surfactants the betaine compounds corresponding to general formula (I),

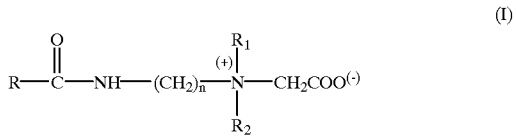

in which R is a long $C_7$–$C_{24}$ alkyl or alkenyl chain; $R_1$ and $R_2$ are, independently, short-chained $C_1$–$C_4$ alkyl; and n is a value from 1 to 5, stand out owing to their interest and their broad industrial and commercial use. Of the betaines included in general formula (I), those which have major industrial significance are the ones in which $R_1$ and $R_2$ are methyl and n is equal to 3.

The betaine compounds mentioned possess, in addition to outstanding detergent power, excellent dermal compatibility characteristics which means that they are currently widely used in the manufacture of a large number of products for cleaning and personal hygiene that require contact with the human skin, such as for example shampoos, liquids and gels for the bath and shower or for washing the hands, washing-up liquids, etc.

It has been well known for some time that the betaines of general formula (I) may be prepared industrially by means of processes based on the sequence of chemical reactions represented in Diagram:

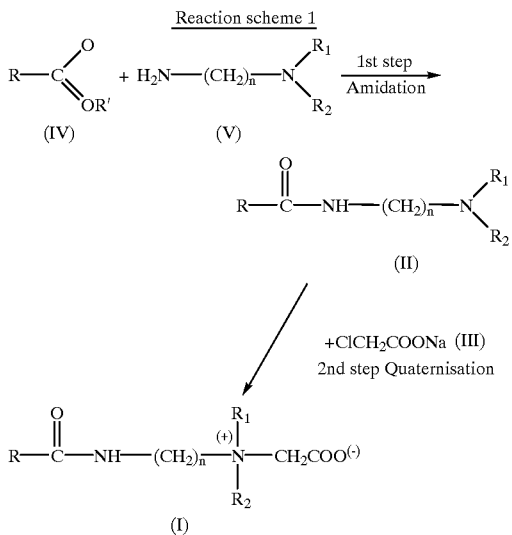

in which R' denotes a hydrogen atom or an alkyl group and the remaining variable substituents R, $R_1$, $R_2$ and n have the values already set out for the general formula (I), such that the starting product (IV) may be a fatty acid or a fatty acid ester, including fatty acid esters with polyhydroxy compounds such as for example the mono, di or triglycerides.

Thus, in a first amidation step the starting diamine (V) is reacted with the fatty acid or any of its esters (IV) to obtain as an intermediate the amidoamine (II) which, in a second quaternisation step, is reacted with monochloroacetic acid or a salt thereof (III) to obtain the betaine compound (I).

The manufacturer of consumer goods such as shampoos, bath and shower liquids or gels, washing-up liquids etc. prefers to use as a raw material liquid aqueous betaine-type surfactant compositions which can readily be mixed with the other components to obtain his finished products. In addition, it is preferable that the said aqueous betaine-type surfactant compositions have a high concentration, greater than 40% and preferably of the order of 50% or more, expressed as percentages by weight of dry residue, since this reduces transport and storage costs and enables any desired degree of dilution to be obtained in the finished consumer product.

For the surfactant manufacture, however, the manufacture of such concentrated betaine-type surfactant compositions creates serious problems in maintaining the flowable liquid state thereof with a suitable viscosity, owing to the tendency of betaines to increase the viscosity of aqueous compositions and to gel them at conventional transport and storage temperatures.

Numerous proposals are known for trying to solve this problem, for example those described in the following patents or patent applications: U.S. Pat. No. 4861517, EP-B-0353580, EP-B-0560114, corresponding to U.S. Pat. No. 5354906, EP-A-0647613, corresponding to U.S. Pat. No. 5464565, WO-A-9512571, WO-A-9514658, EP-A-0656346, WO-A-9524377, EP-A-0677509 and DE-C-19505196, corresponding to WO-A-9625389.

Most of the said documents relate to the incorporation, before or after the above-mentioned second reaction step (quaternisation), of different additives (non-ionic surfactants, free fatty acids, trimethylglycine and other betaines, quaternary ammonium compounds, alkaline earth metal hydroxides etc.) which help to fluidize the concentrated compositions.

In relation to the present invention it is worth while citing the European Patent EP-B-0560114 (Goldschmidt), which describes betaine-type surfactant compositions with a dry residue or solid content of at least 40 wt % which are characterised by containing as fluidizing agent 1% to 3% of $C_8$–$C_{18}$ saturated or $C_8$–$C_{24}$ unsaturated free fatty acids. In addition, German Patent DE-C-19505196 (Henkel), which describes the same type of compositions in which the fluidizing additives, are very varied types of nitrogen-containing compounds, including the mono or diamides of fatty acid dimers, may also be mentioned.

The large quantity of patents and patent applications on the problem of the fluidity of concentrated betaine compositions, most of them very recent, indicates that the technical problem posed allows a large number of novel and inventive solutions, since each of the techniques described has its disadvantages and limitations. Thus, the solution described in the above-mentioned Goldschmidt patent poses the problem that the fluidizing effect of the free fatty acids is rather limited, which creates manufacturing and stability problems and makes it impossible to achieve compositions with good fluidity when a concentration in the region of 50% dry residue or solid content is desired.

OBJECT OF THE INVENTION

The main object of the present invention is to obtain a concentrated aqueous betaine-type surfactant composition or compositions corresponding to the above-mentioned general formula (I), with a dry residue content or solid content of at least 40 wt %, preferably more than 48 wt %, which maintain excellent properties at these concentrations with respect to low viscosity and low gel point.

An additional object of the present invention is a process for the preparation of the said betaine-type surfactant compositions.

DESCRIPTION OF THE INVENTION

In accordance with the present invention, the aqueous betaine-type surfactant compositions of general formula (I),

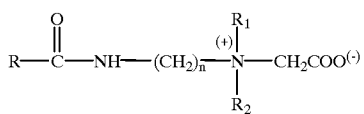
(I)

in which R is a long $C_7$–$C_{24}$ alkyl or alkenyl chain; $R_1$ and $R_2$ are, independently, short-chained $C_1$–$C_4$ alkyl; and n is value from 1 to 5, contain a dry residue of at least 40 wt %, preferably more than 48 wt %, and are characterised in that they contain, by way of fluidizing additives, proportions of from 0.5 to 3.5 wt %, based on the total weight of the composition, of:

i) dimers of fatty aids, and/or
ii) phosphoric esters of fatty alcohols or polyethoxylated fatty alcohols of the general formula

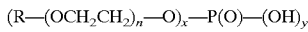

in which R is a $C_8$–$C_{24}$, linear or branched alkyl or alkenyl chain; n is a number from 0 to 10; x and y, independently, may assume the values of 1 or 2, such that the sum of x and y must always be equal to 3,
in addition to other optional components as conventionally used by the expert in formulations of this type.

Betaines
Among the betaines of general formula (I), betaines corresponding to the general formula (Ip)

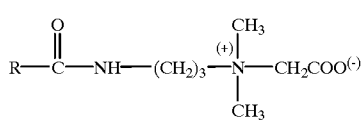
(Ip)

in which R has the meaning explained above, are particularly indicated, those in which R is a saturated $C_7$–$C_{22}$ alkyl chain, such as for example those arising from the use of fatty acids or their glycerides, of hydrogenated coconut or of hydrogenated tallow, being particularly preferred.

R has 7 to 24 carbon atoms, and may have 8 to 24 carbon atoms.

The betaines in question are prepared by means of the process already discussed.

Fluidizing additives
i) Fatty acid dimers
These are dicarboxylic acids produced from the condensation of two molecules of an unsaturated fatty acid, preferably oleic acid, such that the number of carbon atoms for each molecule of dimeric acid is 36, since the starting oleic acid has 18 carbon atoms. Fatty acid dimers are generally accompanied by other acids with a different degree of polymerisation, for example $C_{54}$ trimers, or products originating from the process for their preparation and from the type of oil used as the starting product, for example $C_{27}$ dicarboxylic acids, as well as the starting fatty acids themselves. For the object of the present invention it is preferable for the fatty acid dimers to contain more than 60% of $C_{36}$ dimers, less than 1 wt % of non-dimerised fatty acids, less than 10% of $C_{27}$ dicarboxylic acids and less than 30% of $C_{54}$ fatty acid trimers.

It is particularly preferable for the object of the present invention for the fatty acid dimers to contain more than 70% of $C_{36}$ dimers, less than 0.1 wt % of non-dimerised fatty acids, less than 7% of $C_{27}$ dicarboxylic acids and less than 23% of $C_{54}$ fatty acid trimers.

The fatty acid dimers may, for example, be prepared in accordance with the process described in European Patent Application EP-A-0471566, although they are readily found on the market, for example the products marketed by Unichema International under the name of PRIPOL®, for example those marketed with the references PRIPOL® 1009 and PRIPOL® 1017.

ii ) Phosphoric esters of fatty alcohols or polyethoxylated fatty alcohols.

These are the product of the reaction of fatty acid alcohols or ethoxylated fatty alcohols with phosphorus pentoxide, according to the following reaction diagram:

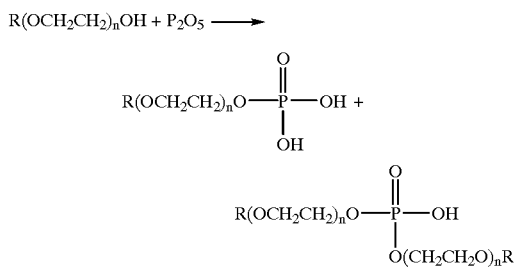

in which the variable R represents a linear or branched $C_8$–$C_{24}$ alkyl or alkenyl chain and n is a number from 0 to 10.

So then, the above-mentioned esters consist of a mixture of mono and disubstituted phosphoric esters in which the respective proportions may be very variable, although those in which the proportion of monosubstituted phosphoric esters to disubstituted phosphoric esters is equal to or greater than 50/50 are preferred.

Phosphoric esters of fatty alcohols or polyethoxylated fatty alcohols have been known for a long time and are commercially available, for example the products marketed by KAO Corporation under the names of MAP of FOSFO-DET®.

Other optional components
One optional component which may be present in the compositions according to the invention, in proportions of from 0% to 4%, is glycerol. This happens when any glyceride of the corresponding fatty acids is used as starting product (IV) according to Diagram 1. In these cases the glycerol released in the reaction remains as an additional component in the final composition. Its effect is not harmful but, on the contrary, the glycerol contributes towards obtaining a suitable viscosity.

The compositions according to the invention may also contain as by-products of the chemical reactions up to 1 wt % of the intermediate aminoamide (II) (see Diagram 1), free fatty acids in proportions of from 0% to 3% and sodium chloride in a proportion of from 0% to 8%.

It should be understood that the possible presence of free fatty acids in the compositions according to the invention would, in any case, be due to their formation during the chemical process and/or to unreacted residues thereof and not to their deliberate addition to the said compositions, since the fluidizing effect thereof is substantially due to the essential additives of the compositions of the invention. In this sense, at any rate, the compositions of the invention which contain a proportion of less than 1 wt % of free fatty acids are preferred.

It will be obvious to any expert that the compositions according to the invention may optionally have added to them any other component of those known for their usefulness in this field of the art, for example any of those described in the patents or patent applications U.S. Pat. No 4,861,517, EP-B-0353580, EP-A-0560114, EP-A-0647613, WO-A-9512571, WO-A-9514658, EP-A-0656346, WO-A-9524377, EP-A-0677509 and DE-C-19505196 mentioned above.

The acidity of the compositions according to the invention is preferably adjusted to a pH range of from 4.5 to 5.5.

The compositions according to the invention are prepared by means of the addition of one of the fluidizing additives
  i) dimers of fatty acids, and/or
  ii) phosphoric esters of fatty alcohols or polyethoxylated fatty alcohols
or mixtures thereof, before or after or during the quaternisation reaction of the amidoamine of formula (II)

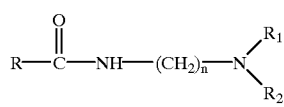

(II)

in which R, $R_1$, $R_2$ and n may have the values indicated above, with monochloroacetic acid or a salt thereof.

The fluidizing additives are preferably added before the quaternisation reaction takes place, before or after proceeding with the incorporation of the amidoamine and the monochloroacetic acid or a salt thereof, and, where the additive consists of the fatty acid dimers, it is preferably added together with a portion of the amidoamine before proceeding with the incorporation of the sodium monochloroacetate and the rest of the amidoamine.

The less concentrated compositions may also be prepared by diluting with water more concentrated compositions prepared by means of the process described above.

The amidoamine of formula (II) is prepared prior to the quaternisation reaction, by conventional methods, by reacting fatty acids or their esters (IV), particularly their glycerides, with the diamine (V), as set out in Diagram 1.

The reaction conditions, both for the formation of the amidoamine and for the quaternisation reaction, are the usual ones known by the expert for the synthesis of this type of betaines.

The compositions according to the invention thus prepared may reach concentrations of up to at least 52% dry residue, presenting the appearance of transparent liquids with good fluidity at ambient temperature and even at temperatures of between 0° C. and room temperature, and their gel point is consistent with these facts. On the other hand, compositions based on the use of free fatty acids as fluidizing agents, such as those described in European Patent EP-B-0560114, do not allow these levels of concentration to be reached without suffering considerable increases in the viscosity and gel point and, in addition, they are made much more difficult to prepare owing to industrial problems derived from their high viscosity and foam generation.

Physical properties of materials used in the invention can be determined by the following ways:

1. The dry residue is determined in a conventional way by weighing, percent by weight, the solid matters that have been left at 105° C. for 2 hours with sodium sulfate.

2-1. The free fatty acids are determined by extracting a phase of petroleum ether from a hydroalcoholic solution which has been adusted to be acidic, drying the phase, converting it to methyl ester thereof and determining the amount of free fatty acids by way of gas chromatography with methyl arachidate as internal standard.

2-2. The dimers of fatty acids are determined by extracting a phase of petroleum ether from a hydroalcoholic solution which has been adjusted to be acidic, drying the petroleum ether phase, determining acid value of the phase and subtracting the amount of the free fatty acids therefrom.

3. Glycerol is determined a usual way with iodometric titration (periodic acid method).

4. The gel point is determined by observing a point showing no fluidity of the solution while the solution contained in a glass tube is cooled in a cooling bath.

5. The free amidoamine is determined by gas chromatography.

6. A mixture of MAP (monoalkyl phosphate) and DAP (dialkyl phosphate) is determined in view of their weight proportions by potentiometric titration.

Thus, a better illustration of the present invention, the following examples are set out below but they should not be considered as limitations to the scope of the object thereof.

EXAMPLE

Example 1

Preparation of the amidoamine (II) from a fatty acid triglyceride

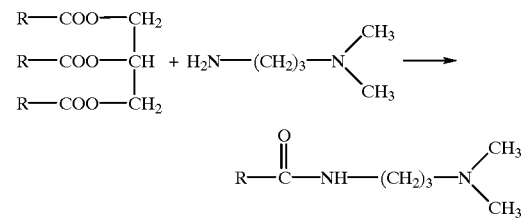

R = hydrogenated coconut 417 g of dimethylaminopropylamine and 837 g of hydrogenated coconut oil are mixed in a 2-liter reaction flask equipped with a stirrer, a temperature probe and an inert gas inlet. The mixture is heated up to 150° C. and maintained under these conditions with reflux until the ester content (expressed as methyl laurate) is less than 2%. At this point, the excess amine is eliminated by vacuum distillation until the dimethylaminopropylamine is less than 200 ppm.

A product is obtained with a total amine value of 171.3 mg KOH/g, and an ester content of 0.5% (equivalent to a saponification index of 1.3 mg KOH/g).

Example 2

Preparation of the amidoamine (II) from fatty acid

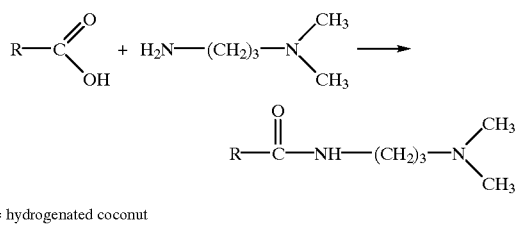

R = hydrogenated coconut 2003 g of hydrogenated coconut fatty acid is fed into a 5-liter reaction flask equipped with a stirrer, a temperature probe and an inert gas inlet. The acid is heated to 1500° C. and 1075 g of dimethylaminopropylamine is added. The reaction conditions are maintained, distilling the water of amidation, until the acid value is less than 5 mg KOH/g. At this point, the excess amine is eliminated by vacuum distillation until the dimethylaminopropylamine is less than 200 ppm.

A product is obtained with a total amine value of 189.5 mg KOH/g, and an acid value of 4.5 mg KOH/g.

Example 3

Preparation of a betaine composition with a fatty alcohol phosphoric ester as fluidizing additive

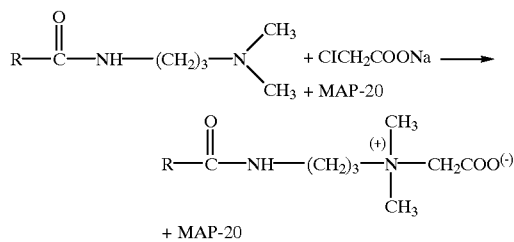

R = hydrogenated coconut 370 g of water, 10 g of 50% sodium hydroxide solution and 22.5 g of MAP-20 (phosphoric ester of lauryl alcohol with ratio of monosubstituted phosphate to disubstituted phosphate of 75:25, marketed by KAO Corporation), corresponding to 3% based on the total feed, are fed into a 1-liter reaction flask equipped with a stirrer, a temperature probe and a pH electrode. The mixture is heated to 60° C. until the additive is completely incorporated. 100.6 g of sodium monochloroacetate and 158 g of the amidoamine prepared in Example 1 are then fed in and the mixture is heated to 80° C. Once all the reagents are incorporated, a further 93.9 g of amidoamine is added in 1 hour. On completion of the addition, the pH is adjusted to a value of 8.5 with 50% sodium hydroxide and the pH and temperature conditions are maintained for 8 hours. After this time the residual amidoamine content is 0.2% and the reaction is considered finished. The product is neutralised with 37% hydrochloric acid until a pH value of 5.2 is reached.

A composition is obtained which is liquid and transparent at room temperature with the following characteristics (percentages wt %):

| | |
|---|---|
| Dry residue | 50.2% |
| Sodium chloride | 6.9% |
| Glycerol | 3.0% |
| Brookfield viscosity (20° C.) | 466 mPa · s |
| Gel point | 12° C. |

Example 4

Preparation of a betaine composition with a fatty acid dimer as fluidizing additive

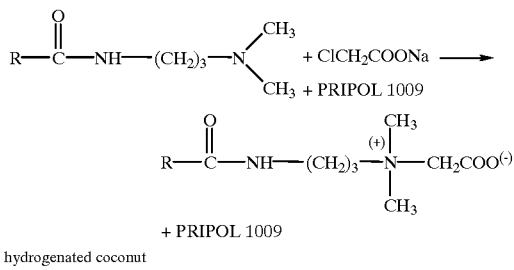

R = hydrogenated coconut 180 g of the amidoamine prepared in Example 1 and 18.8 g of PRIPOL® 1009 fatty acid dimer supplied by Unichem International, corresponding to 2.5% based on the total feed, are fed into a 1-liter reaction flask equipped with stirrer, a temperature probe and a pH electrode. 375 g of water and 103.5 g of sodium monochloroacetate are added to mixture. The mixture is heated to 80° C. and a further 72.7 g of amidoamine is added in 30 minutes. On completion of the addition, the pH is adjusted to a value of 8.5 with 50% sodium hydroxide and the pH and temperature conditions are maintained for 8 hours. After this time the residual amidoamine content is 0.1% and the reaction is considered finished. The product is neutralised with 37% hydrochloric acid until a pH value of 5.1 is reached.

A product is obtained which is liquid and transparent at room temperature with the following characteristics (percentages wt %):

| | |
|---|---|
| Dry residue | 50.5% |
| Sodium chloride | 6.9% |
| Glycerol | 3.0% |
| Brookfield viscosity (20° C.) | 478 mPa · s |
| Gel point | −2° C. |

Examples 5 to 10

Other compositions of the present invention

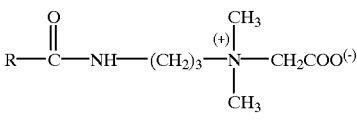

R = hydrogenated coconut shown in Table 1 are prepared in the same way as described in the above Examples, or by means of diluting compositions previously prepared.

TABLE 1

|  | Example 5 | Example 6 | Example 7 | Example 8 | Example 9 | Example 10 |
|---|---|---|---|---|---|---|
| MAP-20 (wt %) | 2.0 | — | — | 3.0 | — | — |
| PRIPOL 1009 (wt %) | — | 2.0 | 3.0 | — | 2.5 | 3.0 |
| Glycerol (wt %) | 3.0 | 3.0 | 3.0 | — | 3.0 | — |
| Dry residue (wt %) | 47.4 | 49.3 | 50.2 | 45.5 | 52.3 | 46.9 |
| $\eta 20°$ C. (mPa · s) | 167 | 428 | 411 | 239 | 1370 | 347 |
| $\eta 20°$ C. 3 months (mPa · s) | 157 | 421 | 291 | 227 | 1240 | 334 |
| Gel point (° C.) | <−10 | 10 | <−10 | 12 | 16 | −6 |
| pH | 4.8 | 4.8 | 5.3 | 5.1 | 4.8 | 5.1 |
| Appearance | transparent liquid with good fluidity | transparent liquid with good fluidity | transparent liquid with good fluidity | transparent liquid with good fluidity | transparent liquid with good fluidity | transparent liquid with good fluidity | in which MAP-20 and PRIPOL 1009 have the meaning already discussed in the above examples and the viscosities (I) are determined by the Brookfield system.

As may readily be deduced from the results obtained in Examples 2 to 10, the compositions of the invention may contain at least up to 52 wt % of dry residue without any significant loss of their appearance or of their good fluidity.

Comparative example 1

Composition with free fatty acid as fluidizing additive

A composition is prepared in the same way as in Example 4, calculated to contain 51 wt % of dry residue and in which the 2.5% of PRIPOL 1009 is substituted by 2.5% of lauric acid.

A large increase in viscosity is produced during the process and a large quantity of foam is formed which make the industrial preparation of the composition non-viable.

Comparative example 2

Glycerol-free composition with free fatty acid as fluidizing additive

Starting from the amidoamine prepared in Example 2 and following the method described in Example 4, a glycerol-free composition is prepared, calculated to contain 47 wt % of dry residue and in which the 3.0% of PRIPOL 1009 is substituted by 3% of lauric acid.

In this case too, the increase in viscosity and the formation of foam make the industrial preparation of the composition non-viable.

The results obtained in the comparative examples show quite clearly the advantages of the fluidizing additives of the compositions according to the invention compared with the fatty acids described for the same function in European Patent EP-B-0560114.

Anything which does not affect, impair, change or modify the essence of the compositions described can be varied for the purposes of this patent.

What is claimed is:

1. A concentrated aqueous betaine surfactant composition comprising a betaine compound having the formula (I):

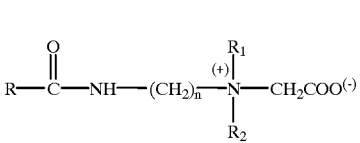

(I)

in which R is a $C_7$–$C_{24}$ alkyl or alkenyl chain; $R_1$ and $R_2$ are, independently, a $C_1$–$C_4$ alkyl; and n is a number of from 1 to 5;

and from 0.5 to 3.5 wt %, based on the total weight of the composition, of a fluidizing additive which is (i) a fatty acid dimer composition and, as an optional fluidizing additive (ii) phosphoric esters of fatty alcohols or polyethoxylated fatty alcohols, having the formula

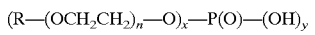

in which R is a $C_8$–$C_{24}$ alkyl or alkenyl chain being linear or branched; n is a number of from 0 to 10; and x and y are independently, a number of 1 or 2, provided that the sum in total of x and y is equal to 3, and the composition containing a solid content of at least 40 wt %.

2. The composition as claimed in claim 1, in which the betaine compound has the formula (Ip):

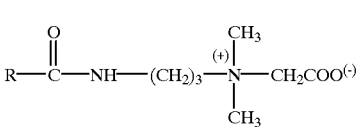

(Ip)

in which R is a saturated $C_7$–$C_{22}$ alkyl chain.

3. The composition as claimed in claim 1, wherein the fatty acid dimer composition contains more than 60% of $C_{36}$ dimers, less than 1 wt % of non-dimerised fatty acids, less than 10% of $C_{27}$ dicarboxylic acids and less than 30% of $C_{54}$ fatty acid trimers.

4. The composition as claimed in claim 1, wherein the fatty acid dimer composition contains more than 70% of $C_{36}$ dimers, less than 0.1 wt % of non-dimerised fatty acids, less than 7% of $C_{27}$ dicarboxylic acids and less than 23% of $C_{54}$ fatty acid trimers.

5. The composition as claimed in claim 1, wherein the fluidizing additive includes (ii) the phosphoric esters of fatty alcohols or polyethoxylated fatty alcohols which are a mixture of mono- and di-substituted phosphoric esters in which a proportion of the mono-substituted phosphoric esters to the di-substituted phosphoric esters is not less than 50/50.

6. The composition as claimed in claim 1, which further comprises up to 4 wt % of glycerol.

7. The composition as claimed in claim 1, which further comprises less than 1 wt % of free fatty acids.

8. A process for preparing the composition as defined in claim 1, which comprises the steps of adding an appropriate quantity of the fluidizing additives, before or after or during the quaternisation reaction of an amidoamine having the formula (II):

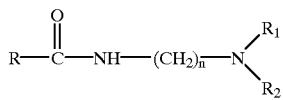

(II)

in which R, $R_1$, $R_2$ and n are defined in claim 1, with monochloroacetic acid or a salt thereof, so that the final composition contains 0.5 to 3.5 wt % of fluidizing additive.

9. The process as claimed in claim 8, in which the fluidizing additive is added before the quaternisation reaction takes place.

* * * * *